(12) United States Patent
Williams

(10) Patent No.: US 6,536,260 B2
(45) Date of Patent: Mar. 25, 2003

(54) BALLOON CATHETER LEAK DETECTION METHOD AND APPARATUS

(75) Inventor: Jonathan Williams, Montville, NJ (US)

(73) Assignee: Datascope Investment Corp., Montvale, NJ (US)

( * ) Notice: Subject to any disclaimer, the term of this patent is extended or adjusted under 35 U.S.C. 154(b) by 0 days.

(21) Appl. No.: 09/903,447

(22) Filed: Jul. 11, 2001

(65) Prior Publication Data

US 2001/0035046 A1 Nov. 1, 2001

Related U.S. Application Data

(63) Continuation-in-part of application No. 09/339,492, filed on Jun. 24, 1999, now abandoned.

(51) Int. Cl.[7] .......................... G01M 3/00; A61N 1/362
(52) U.S. Cl. .................................. 73/40; 73/52; 600/18
(58) Field of Search .................... 73/40, 52; 345/24; 600/17, 18, 505, 486

(56) References Cited

U.S. PATENT DOCUMENTS

| | | | | | |
|---|---|---|---|---|---|
| 3,359,974 A | * | 12/1967 | Khalil | .......................... | 600/526 |
| 3,698,381 A | * | 10/1972 | Federico et al. | ............... | 600/17 |
| 3,720,199 A | * | 3/1973 | Rishton et al. | ................ | 600/18 |
| 4,175,264 A | * | 11/1979 | Schiff | ........................... | 345/24 |
| 4,522,194 A | * | 6/1985 | Normann | ...................... | 600/18 |
| 4,969,470 A | * | 11/1990 | Mohl et al. | .................. | 600/486 |
| 5,242,374 A | * | 9/1993 | Isoyama et al. | ............... | 600/18 |
| 5,513,956 A | * | 5/1996 | Lewis et al. | ................... | 417/12 |
| 5,720,293 A | * | 2/1998 | Quinn et al. | ................. | 600/505 |
| 6,098,405 A | * | 8/2000 | Miyata et al. | ................ | 60/535 |

* cited by examiner

Primary Examiner—Daniel S. Larkin
Assistant Examiner—Jay L Politzer
(74) Attorney, Agent, or Firm—Abraham Ronai

(57) ABSTRACT

An intra-aortic balloon pump system having a leak detector comprising a processor, a pressure sensor, and optionally a temperature sensor. Gas leaks from the intra-aortic balloon pump system are detected by comparing shuttle gas pressure readings, taken just prior to IAB inflation, with similar thermodynamic histories, i.e. similar equilibrium times.

18 Claims, 1 Drawing Sheet

BALLOON CATHETER LEAK DETECTION METHOD AND APPARATUS

RELATED APPLICATIONS

This application is a continuation-in-part application of application Ser. No. 09/339,492, filed on Jun. 24, 1999 now abandoned, herein incorporated by reference.

BACKGROUND OF THE INVENTION

1. Field of the Invention

The invention relates to a leak detector for a pressurized device. More particularly, the invention relates to a detector for detecting a gas leak from an intra-aortic balloon ("IAB") catheter system.

1. Description of the Prior Art

In counterpulsation therapy, a long cylindrical intra-aortic balloon is inserted percutaneously into a patient's femoral artery. The balloon is then advanced until it is located in the descending aorta. Once in place, the balloon is inflated and deflated anti-phase to the pumping action of the patient's left ventricle, i.e. the balloon is held inflated during at least a portion of diastole and is held deflated during at least a portion of systole. The IAB catheter is connected to a pump (IABP) for inflation and deflation of the balloon membrane on the distal end of the catheter.

IAB therapy is most effective when the transitions between the inflated and deflated states of the balloon membrane are rapid, typically, less than 0.1 second. When inflated and deflated in this manner, coronary blood flow is increased and cardiac work is decreased. This lifesaving therapy supports the heart during ischemic events or cardiogenic shock.

When sized for adult patients, the IAB balloon typically has a volume of 40 cubic centimeters. A small diameter catheter having an outside diameter of less than 0.1 inches (2.5 mm) is integral to the IAB. The catheter provides pneumatic access to the IAB. By design, the catheter's diameter is small to reduce its impact upon blood flow in the patient's femoral artery. As a result, the catheter's small internal diameter impedes the flow of shuttle gas to and from the IAB balloon. Also, the catheter's pressure drop at the catheter and balloon junction is large because the gas velocity in the catheter is high, approximately 500 ft/sec.

To reduce the impact of these effects: (1) helium gas is used as the working (shuttle) gas to inflate and deflate the IAB; and (2) a larger diameter "extension" catheter is used to interconnect the IAB's catheter to the intra-aortic balloon pump's pneumatic port. The extension catheter's diameter is larger, and thus, it's pressure drop is lower.

During the pumping process, the shuttle gas is pressurized and de-pressurized each heartbeat by the IAB pump. The sources of the pressure changes are the pump and the restriction of the IAB's catheter. As a thermodynamic consequence, on each inflation of the IAB, heat energy is stored in the shuttle gas, and on each deflation, heat is released.

Consequently, after each inflation or deflation event, the shuttle gas pressure changes as it attempts to thermally equilibrate with its environment. Typically, the pressure decays toward the appropriate average shuttle pressure in an exponential manner with a time constant on the order of approximately 1 second.

During IAB therapy, thermal equilibrium is not achieved because the durations of IAB inflation and deflation are too brief, i.e. the shuttle gas is re-compressed before it "recovers" from deflation and vice versa. The durations of the deflate and inflate intervals, are approximately 0.375 seconds at a typical patient heart rate of 80 beats per minute. The duration of the deflate interval is defined as the duration the balloon remains in the deflated state during systole plus the amount of time it takes for the balloon to deflate. The duration of the inflate interval is defined as the duration the balloon remains in the inflated state during diastole plus the amount of time it takes for the balloon to inflate.

If the shuttle gas leaks out of the IABP system, the IAB will not fully inflate. This diminishes therapy and can be harmful if gas is lost to the patient's blood stream. Accordingly, there is a need for detection of gas leaks from the IAB system's shuttle gas system. Detection systems have been incorporated into most existing IABP systems.

In principle, detection of gas loss appears straightforward. In accordance to the Ideal Gas Law, the quantity (mass) of a gas in a known volume can be determined by measurement of its static pressure, and temperature.

Accordingly, for leak detection using the Ideal Gas Law, IABP systems have a shuttle gas pressure sensor. To meet the Law's "known volume" requirement, the shuttle gas pressure is measured when the IAB is in its deflated state. This assures that the gas resides in the more stable and predicable geometries of the catheter(s) and intra-aortic balloon pump's drive.

To meet the Law's static pressure criteria, the shuttle gas pressure is measured as "late" as possible after IAB deflation. This maximizes the time interval available for IAB deflation. When the IAB is fully deflated, the shuttle gas is no longer moving and the "static" criteria is met. This corresponds to measuring the pressure just prior to IAB inflation.

The Law's final criteria, measurement of shuttle gas temperature, is more difficult to adequately satisfy. This is because the shuttle gas temperature is the sum of two components, a local ambient temperature component and a thermal transient component, due to gas compression and decompression. Temperature sensors with the necessary speed of response to measure the thermal transients are fragile and expensive. For this reason, shuttle temperature is not measured by most IAB systems.

When the Ideal Gas Law is used for leak detection, and the effect of temperature is ignored, it is mathematically equivalent to assuming that the gas temperature is constant. In the case of local ambient temperature (average shuttle gas temperature), this is likely to be true if leak detection comparisons are limited to readings which were taken close in time. This is true if one presumes that the ambient's effect upon the average temperature of the shuttle gas is slow, i.e. on the order of minutes.

However, in the case of the thermal transient component, it is not sufficient to compare heartbeats taken at similar times. An additional criteria must be added to avoid false alarms. This is a consequence of the thermal transient's effect upon shuttle gas pressure. Specifically, after the gas is decompressed, its pressure exponentially decays toward the average shuttle gas pressure level. Typically, a leak detection pressure measurement is taken before this decay process is complete. As a result, the pressure reading has a transient component whose value depends upon the time when the reading was taken, relative the decompression event. Comparisons of pressure readings with different decay times result in false leak detection alarms, unless the alarm's limits are made larger, and thus less sensitive, to exclude these errors.

Gas loss alarms can be absolute or relative. An absolute alarm compares the current gas pressure against a fixed pressure limit. To avoid false alarms due to the variability of temperature and volume, the absolute alarm limits must be large, on the order of three to five cubic centimeters per hour.

U.S. Pat. No. 3,698,381, issued to Federico et al., is an example of an absolute alarm system. Frederico et al. disclose an absolute leak detection method for an intra-aortic balloon catheter which involves monitoring the pressure of the shuttle gas just prior to inflation of the balloon. Leaks are detected on a beat-to-beat basis by comparing the measured pressure to fixed alarm limits. If the pressure of any single heartbeat is outside the fixed alarm or prescribed limits an alarm is declared. As discussed, the leak detection disclosed by Federico et al. is likely to cause false alarms because the effect of temperature is completely ignored.

A "relative" or differential gas alarm checks for gas loss from a known datum. The datum is an initial shuttle gas pressure measurement taken when the system is deemed leak free. After this initial datum is taken it is compared to subsequent pressure readings to determine if gas loss has occurred. An alarm is issued if the difference between the datum and a new reading exceeds a predefined limit.

The sensitivity of a relative gas alarm can be much higher than the absolute alarm because the initial datum implicitly includes the effects of current ambient temperature. This initial datum also implicitly captures the effect of tolerance of volumes. However, unless proper steps are taken, it does not include the effect of the thermodynamic temperature transient component induced by pumping.

The present invention comprises a differential leak detection method for an IAB catheter for detecting the loss of shuttle gas due to an IAB perforation. Perforations are typically due to abrasion of the IAB membrane by aortic plaque, and occur after an initial, leak free interval of pumping. The detection method accounts for the effects of the thermodynamic temperature transient induced by pumping by comparing shuttle gas pressure readings, taken just prior to IAB inflation, with similar thermodynamic histories, i.e. similar equilibrium times.

SUMMARY OF THE INVENTION

Accordingly, it is an object of the invention to produce a leak detector for an IAB system capable of making an accurate leak detection, by measuring changes in the gas pressure, despite thermodynamic variations in the shuttle gas temperature and the mechanical tolerances on pump volumes.

The invention is a leak detector for an intra-aortic balloon pump system comprising a processor, a pressure sensor, and optionally a temperature sensor. Gas leaks from the intra-aortic balloon pump system are detected by comparing shuttle gas pressure readings, taken just prior to IAB inflation, with similar thermodynamic histories, i.e. similar equilibrium times.

To the accomplishment of the above and related objects the invention may be embodied in the form illustrated in the accompanying drawings. Attention is called to the fact, however, that the drawings are illustrative only. Variations are contemplated as being part of the invention, limited only by the scope of the claims.

BRIEF DESCRIPTION OF THE DRAWINGS

In the drawings, like elements are depicted by like reference numerals. The drawings are briefly described as follows.

DETAILED DESCRIPTION OF THE PREFERRED EMBODIMENTS

Figure 1:
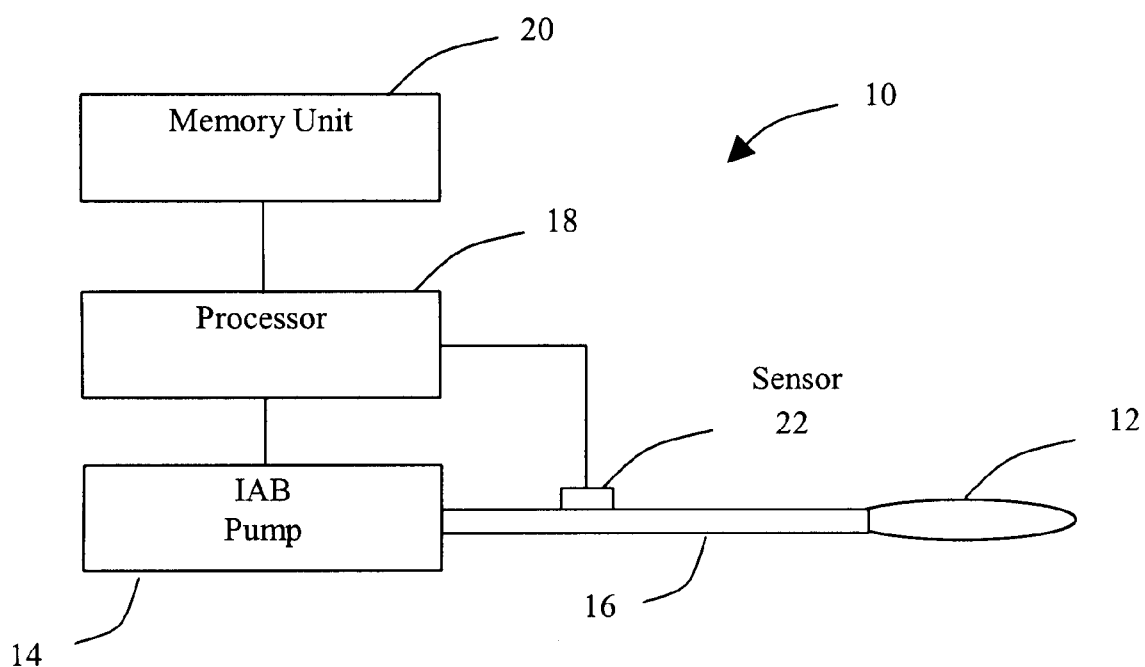
FIG. 1 is block and partly schematic diagram of the present invention.

FIG. 1 illustrates a block diagram of the present invention, generally designated 10, comprising an intra-aortic balloon 12, an intra-aortic balloon pump 14, an intra-aortic balloon catheter 16 connecting said intra-aortic balloon pump 14 and said intra-aortic balloon 12, a processor 18 connected to said intra-aortic balloon pump 14, a memory unit 20 and a sensor 22 both connected to the processor 18. Processor 18 can take the form of a computer, a more simplified circuit or control device, or can be part of the control device built into the intra-aortic balloon pump 14. The intra-aortic balloon pump 14 shuttles a gas, generally helium, back and forth into the intra-aortic balloon 12. For each heartbeat of a patient, a pressure reading is taken by sensor 22 preferably just prior to the inflation of intra-aortic balloon 12. This timing of the reading allows for the longest amount of time for the shuttle gas pressure to stabilize, i.e. achieve static conditions and thermal equilibrium. This timing also assures that the volume of shuttle gas is known because at this time the shuttle gas resides in mechanical elements of known geometry, i.e. intra-aortic balloon pump 14 and intra-aortic balloon catheter 16. Pressure measurements can be taken at other points in time but it is preferred that they are taken at the same point in each inflate/deflate cycle of intra-aortic balloon 12.

The pressure readings are stored in memory unit 20. Affiliated data may also stored in memory unit 20, including but not limited to the inflate and deflate durations of intra-aortic balloon 12 and the time of occurrence of the heartbeat. The duration of the deflate interval is defined as the duration the balloon remains in the deflated state during systole plus the amount of time it takes for the balloon to deflate. The duration of the inflate interval is defined as the duration the balloon remains in the inflated state during diastole plus the amount of time it takes for the balloon to inflate. Processor 18 sorts all of the pressure measurements by the duration of the inflate/deflate intervals from which the pressure measurements were taken. Periodically, processor 18 subtracts "similar" pressure readings, i.e. pressure readings taken from intra-aortic balloon 12 cycles having similar inflate/deflate durations. Processor 18 preferably uses the pressure readings having the most similar inflate/deflate durations. An alarm condition is declared if any of the differences exceed a fixed limit. Also periodically, the processor may eliminate from the memory unit 20 data read from heartbeats that are too old, i.e heartbeats for which the assumption of constant ambient temperature is invalid.

The determination as to whether pressure readings are "similar" may be made by comparing intra-aortic balloon 12 deflate interval durations or preferably both inflate and deflate interval durations.

Inflate/deflate intervals of similar duration have thermal transients of similar amplitude and character. Consequently, when pressure readings from similar interval durations are subtracted, the component of the pressure reading due to transient thermal energy subtracts out. Accordingly, any residual pressure difference is due to a loss of gas. If the pressure difference is found to be excessive, then an alarm is issued.

The more similar the interval durations for the pressure measurements chosen are the more accurate the gas loss determination will be. Accordingly, it is preferred to compare pressure measurements from the most similar interval durations. However, the term "similar" with respect to inflate/deflate interval durations can mean any interval chosen specifically so as to reduce the transient thermal energy component to the pressure measurement. Note that it is preferable to select the longest deflate durations for use in alarm detection because (i) the decay of the thermal transient is more complete and (ii) the gas is more likely to have reached a static state, i.e. the time available for IAB deflation is maximized. Consequently, when pressure readings from long duration heartbeats are compared (subtracted), the residual errors due to these effects are minimized. Similarly, in the event that there is a residual component in the measured pressure due to shuttle gas flow, an additional benefit of this approach is that it also tends to subtract out, provided that identical deflation intervals are subtracted.

The present invention comprises at least two types of gas alarms, namely, a slow gas alarm and a rapid gas alarm. To test for the rapid loss of gas, processor 18 compares "similar" pressure readings that meet two criteria. First, the pressure readings must taken from inflate/deflate intervals of similar duration. Second, the readings are preferably from heartbeats which were captured close in time, e.g. heartbeat data captured within a one to five minute interval or preferably within a one to three minute interval. If the pressure drop between these beats exceed a predetermined alarm limit, then a rapid gas loss event is declared.

The sensitivity of the rapid gas loss alarm is highest for a number of reasons. First, comparing heartbeats of similar duration eliminates the effect of the thermal transient pressure component. Second, comparing heartbeats taken close together in time eliminates the effect of local ambient temperature. When heartbeats taken close together in time are subtracted, the effect of local ambient temperature is eliminated, i.e. it subtracts out. Since the effects of ambient temperature and thermal transients are eliminated, the sensitivity of this alarm exceeds that of a fixed alarm system.

As discussed above, Federico et al. compare pressure readings to a fixed alarm limit, irrespective of their duration or proximity in time. Consequently, to avoid false alarms due ambient temperature and thermal transients, the alarm limit is necessarily larger and thus, less sensitive.

To test for the slow loss of gas, the pressure measurements must be compared over a longer period of time. The pressure measurements, taken from heartbeats of similar duration, are stored and periodically plotted against time by processor 18. The slope of the plot is used as an indicator of the rate of gas loss. Typically, IAB membranes and pump materials are permeable to diffusion of helium. Consequently, there is an expected slow loss of shuttle gas to the diffusion process. A slow gas alarm is issued when either the rate or total amount of shuttle gas loss exceeds the expected limits.

It may also be useful to maintain multiple plots, each plot being computed from data relating to a specific heart rate or narrow range of heart rates. In this case, each plot would provide its own estimate of current slow gas rate.

In current intra-aortic balloon pump systems, the pressure readings are not adjusted for the effects of temperature and also are taken at random points in the inflate/deflate cycle of the intra-aortic balloon 12. The underlying basis of the present device and method disclosed is that when "similar" pressure readings are used, i.e. pressure readings measured at the same point in inflate/deflate intervals of similar durations, the transient temperature effect, due the lack of thermal equilibration, will subtract out.

Given the elimination of the transient thermal pressure component, if the subtraction of pressure readings yields a significant difference it must be due to a gas loss or gain. In the case of the slow gas alarm, pressure readings from heart beats which are not in close proximity in time are compared. Consequently, the alarm is vulnerable to changes in local ambient temperature. For this reason, the slow gas alarm is less sensitive than the rapid gas alarm. Often, the pump's local ambient temperature is relatively constant. In this case, the effects of ambient temperature subtract out.

The sensitivity of the slow gas alarm can be improved by using a temperature sensor (not shown in FIG. 1) to measure local ambient temperature or preferably average shuttle gas pressure. The sensor's reading is then used, in conjunction with the Ideal Gas Law, to compute an adjusted pressure reading for each heart beat. As in the above, the adjusted readings are then stored along with their associated durations and periodically plotted against time by the processor 18. The slope of the plot is used as an indicator of the rate of gas loss. Note that in this case, a fast responding temperature sensor is not required since we are using the temperature readings to correct only for the slow effect of ambient temperature. The effect of thermal transients is excluded by limiting computations and comparisons to measurements of like durations.

Note that it is anticipated to use the present invention for the detection of gas gains, i.e. a leak of gas into the shuttle gas system. This can occur if there is a leak to atmospheric pressure or if there is a leakage into the system due to the failure of one or more IABP 14 helium fill valves (not shown). Note also that the term shuttle gas may also include a fluid or any other medium known in the art useful for inflating and deflating an expandable chamber. In reference to an IAB catheter, Helium is the preferred shuttle gas.

Note also that the present invention is not limited to use with intra-aortic balloon catheters. Any pressurized cardiac assist device having one or more chambers being filled and evacuated of a working fluid, such as gas, may benefit from the enhanced pressure loss or gain sensitivity realized through use of the present invention.

As many apparently widely different embodiments of the present invention can be made without departing from the spirit and scope thereof, it is to be understood that the invention is not limited to the specific embodiments thereof except as defined in the appended claims.

What is claimed is:

1. A leak detector device for an intra-aortic balloon catheter comprising a processor and a pressure sensor communicating with said processor for sensing the pressure of a gas in the balloon catheter, said balloon catheter having a balloon on one end, said balloon being inflated and deflated by a pump, during therapy said balloon being held inflated by the pump during at least a portion of diastole and being held deflated during at least a portion of systole, the processor comparing pressure measurements taken by the pressure sensor from different intra-aortic balloon cycles having similar deflate interval durations and indicating a pressure loss or gain if the pressure measurements vary beyond a predetermined level.

2. A method for detecting a leak in an intra-aortic balloon catheter comprising a processor and a pressure sensor communicating with said processor for sensing the pressure of a gas in the balloon catheter, said balloon catheter having a balloon on one end, said balloon being inflated and deflated by a pump, during therapy said balloon being held inflated by the pump during at least a portion of diastole and being held deflated during at least a portion of systole, comprising the steps of:

a) measuring the pressure in the balloon catheter during two or more inflate/deflate cycles of the balloon;

b) comparing pressure measurements from different inflate/deflate cycles having similar deflate interval durations; and c) indicating a leak if the pressure measurements vary negatively beyond a predetermined amount or a pressure gain if the pressure measurements vary positively beyond a predetermined threshold.

3. A leak detector device for an intra-aortic balloon catheter comprising a processing means and a pressure sensing means communicating with said processing means for sensing the pressure of a gas in the balloon catheter, said balloon catheter having a balloon on one end, said balloon being inflated and deflated by a pump, during therapy said balloon being held inflated by the pump during at least a portion of diastole and being held deflated during at least a portion of systole, the processing means comparing pressure measurements taken by the pressure sensing means from different intra-aortic balloon cycles having similar deflate interval durations and indicating a pressure loss or gain if the pressure measurements vary beyond a predetermined level.

4. A leak detector device for an intra-aortic balloon catheter comprising a processor and a pressure sensor communicating with said processor for sensing the pressure of a gas in the balloon catheter, said balloon catheter having a balloon on one end, said balloon being inflated and deflated by a pump, during therapy said balloon being held inflated by the pump during at least a portion of diastole and being held deflated during at least a portion of systole, the processor comparing pressure measurements taken by the pressure sensor from different intra-aortic balloon cycles having similar inflate interval durations and indicating a pressure loss or gain if the pressure measurements vary beyond a predetermined level.

5. The leak detector as claimed in claim 1 or 4 wherein the processor measures the gas pressure in the balloon catheter at the same point in a plurality of inflation/deflation cycles of the balloon.

6. The leak detector device as claimed in claim 1 or 4 wherein the processor compares pressure measurements taken just prior to inflation of the balloon.

7. The leak detector device as claimed in claim 1 or 4 further comprising a memory unit connected to said processor for storing the pressure measurements.

8. The leak detector device as claimed in claim 1 or 4 wherein the processor compares pressure measurements taken by the pressure sensor from intra-aortic balloon cycles having the most similar interval durations and indicating a pressure loss or gain if the pressure measurements vary beyond a predetermined level.

9. The leak detector device as claimed in claim 1 or 4 wherein the processor compares pressure measurements taken by the pressure sensor from intra-aortic balloon cycles having the longest interval durations and indicating a pressure loss or gain if the pressure measurements vary beyond a predetermined level.

10. The leak detector device as claimed in claim 1 or 4 wherein the processor compares pressure measurements taken by the pressure sensor from intra-aortic balloon cycles having the longest and most similar interval durations and indicating a pressure loss or gain if the pressure measurements vary beyond a predetermined level.

11. The leak detector device as claimed in claim 1 or 4 wherein the processor compares pressure measurements that are taken within five minutes of each other.

12. A method for detecting a leak in an intra-aortic balloon catheter comprising a processor and a pressure sensor communicating with said processor for sensing the pressure of a gas in the balloon catheter, said balloon catheter having a balloon on one end, said balloon being inflated and deflated by a pump, during therapy said balloon being held inflated by the pump during at least a portion of diastole and being held deflated during at least a portion of systole, comprising the steps of:

a) measuring the pressure in the balloon catheter during two or more inflate/deflate cycles of the balloon;

b) comparing pressure measurements from different inflate/deflate cycles having similar inflate interval durations; and c) indicating a leak if the pressure measurements vary negatively beyond a predetermined amount or a pressure gain if the pressure measurements vary positively beyond a predetermined threshold.

13. The method as claimed in claim 1 or 12 wherein the processor measures the gas pressure in the balloon catheter in steps (a) at the same point in a plurality of inflation/deflation cycles of the balloon.

14. The method as claimed in claim 13 or 12 wherein the pressure measurements compared in step (b) are taken just prior to inflation of the balloon.

15. The method as claimed in claim 13 or 12 wherein the pressure measurements compared in step (b) have the most similar durations.

16. The method as claimed in claim 13 or 12 wherein the pressure measurements compared in step (b) have the longest durations.

17. The method as claimed in claim 13 or 12 wherein the pressure measurements compared in step (b) have the longest and most similar durations.

18. A leak detector device for an intra-aortic balloon catheter comprising a processing means and a pressure sensing means communicating with said processing means for sensing the pressure of a gas in the balloon catheter, said balloon catheter having a balloon on one end, said balloon being inflated and deflated by a pump, during therapy said balloon being held inflated by the pump during at least a portion of diastole and being held deflated during at least a portion of systole, the processing means comparing pressure measurements taken by the pressure sensing means from different intra-aortic balloon cycles having similar inflate interval durations and indicating a pressure loss or gain if the pressure measurements vary beyond a predetermined level.

* * * * *